US009632082B2

(12) United States Patent
Ishiguro et al.

(10) Patent No.: US 9,632,082 B2
(45) Date of Patent: Apr. 25, 2017

(54) MOTOR PROTEIN DEVICE

(71) Applicants: TAIYO YUDEN CO., LTD., Tokyo (JP); NAGAOKA UNIVERSITY OF TECHNOLOGY, Niigata (JP)

(72) Inventors: Takashi Ishiguro, Takasaki (JP); Hajime Honda, Nagaoka (JP)

(73) Assignees: TAIYO YUDEN CO., LTD., Tokyo (JP); NAGAOKA UNIVERSITY OF TECHNOLOGY, Niigata (JP)

( * ) Notice: Subject to any disclaimer, the term of this patent is extended or adjusted under 35 U.S.C. 154(b) by 29 days.

(21) Appl. No.: 14/359,727

(22) PCT Filed: Nov. 29, 2012

(86) PCT No.: PCT/JP2012/080873
§ 371 (c)(1),
(2) Date: May 21, 2014

(87) PCT Pub. No.: WO2013/081035
PCT Pub. Date: Jun. 6, 2013

(65) Prior Publication Data
US 2014/0287962 A1 Sep. 25, 2014

(30) Foreign Application Priority Data

Nov. 29, 2011 (JP) ................................. 2011-260832

(51) Int. Cl.
  *G01N 33/558* (2006.01)
  *G01N 33/574* (2006.01)
  *G01N 33/537* (2006.01)

(52) U.S. Cl.
  CPC ......... *G01N 33/558* (2013.01); *G01N 33/537* (2013.01); *G01N 33/57473* (2013.01)

(58) Field of Classification Search
  None
  See application file for complete search history.

(56) References Cited

U.S. PATENT DOCUMENTS

| | | | | | |
|---|---|---|---|---|---|
| 5,830,659 | A | * | 11/1998 | Stewart | ........................ 435/6.11 |
| 2004/0018611 | A1 | * | 1/2004 | Ward et al. | ................ 435/287.2 |

(Continued)

FOREIGN PATENT DOCUMENTS

| JP | A-2005-530517 | 10/2005 |
|---|---|---|
| JP | A-2006-204241 | 8/2006 |

(Continued)

OTHER PUBLICATIONS

Aug. 12, 2016 Office Action issued in Japanese Patent Application No. 2013-547201.

(Continued)

*Primary Examiner* — Rebecca Martinez
(74) *Attorney, Agent, or Firm* — Oliff PLC

(57) ABSTRACT

[Problem] To provide a motor protein device capable of efficiently transporting and detecting a target antibody.
[Solution] A motor protein device of the present invention includes a collection region where a carrier molecule collects a target molecule using antigen-antibody reaction, and an unloading region where the target molecule is unloaded from the carrier molecule using chemical equilibrium. Further, the motor protein device includes a transport path provided between the collection region and the unloading region through which the carrier molecule can transport the target molecule, and an analysis portion which detects a change in concentration of the target molecule in the unloading region. The unloading region includes certain antibody having capture force higher than predetermined antibody being modified to the carrier molecule and the target molecule is concentrated in the unloading region. The carrier molecule includes actin obtained by modifying the predetermined antibody, and the transport path includes immobilized myosin.

12 Claims, 6 Drawing Sheets

(56) References Cited

U.S. PATENT DOCUMENTS

| | | | |
|---|---|---|---|
| 2004/0259149 A1* | 12/2004 | Nicolau | G01N 33/54373 |
| | | | 435/7.1 |
| 2007/0254020 A1 | 11/2007 | Moritani et al. | |
| 2009/0156791 A1 | 6/2009 | Hiyama et al. | |
| 2010/0144556 A1* | 6/2010 | Famouri et al. | 506/30 |

FOREIGN PATENT DOCUMENTS

| | | |
|---|---|---|
| JP | A-2006-288336 | 10/2006 |
| JP | A-2007-111004 | 5/2007 |
| JP | A-2007-296609 | 11/2007 |
| WO | WO 2004/003558 A1 | 1/2004 |

OTHER PUBLICATIONS

Written Opinion issued in International Patent Application No. PCT/JP2012/080873 dated Feb. 19, 2013.
Fischer et al., "A smart dust biosensor powered by kinesin motors," *Nature Nanotechnology*, 2009, vol. 4, pp. 162-166.
Hiyama et al., "Autonomous Loading, Transport, and Unloading of Specified Cargoes by Using DNA Hybridization and Biological Motor-Based Motility," *Small*, 2008, vol. 4, No. 4, pp. 410-415.
International Search Report issued in International Application No. PCT/JP2012/080873 mailed Feb. 19, 2013.
Feb. 28, 2017 Office Action issued in Japanese Patent Application No. 2013-547201.

\* cited by examiner

| | Concentration | | | | | | Measurement unit |
|---|---|---|---|---|---|---|---|
| CEA concentration | 0.1 | 1 | 5 | 10 | 50 | 100 | ng/mL |
| Conventional example (Chemiluminescence method) | ND | 1.02 | 5.04 | 9.99 | 49.5 | 98.5 | ng/mL |
| Example | 0.021 | 0.15 | 0.65 | 1.6 | 6.5 | 10.8 | mV |

MOTOR PROTEIN DEVICE

TECHNICAL FIELD

The present invention relates to a motor protein device that can transport a desired molecule to a destination, and can separate and concentrate the transported molecules.

BACKGROUND ART

Conventionally, in order to efficiently transport a target DNA and the like, a method, a device or the like is known where a microtubule or an actin which interacts with a motor protein is glided on a substrate having an immobilized kinesin or myosin, and a target molecule is collected using these motor protein and the like (refer to Patent Literatures 1 to 3).

In the Patent Literature 1, a technology is described that a carrier molecule associated a single-stranded DNA loaded a molecule as a cargo is glided, and the loaded molecule is unloaded by the formation of a double-stranded nucleotide at a destination.

In the Patent Literature 2, a molecular motor system for collection and purification of the target RNA by using a substrate coated with kynesin and a microtubule associated a binding functional nucleic acid is described.

In the Patent Literature 3, a molecule motor system for moving a target DNA selectively using a probe DNA conjugated microtubule and a substrate coated with kynesin is described.

Further, in order to detect that a target molecule is transported to a predetermined region, a method of detecting optically by providing a fluorescent label or the like on a carrier molecule is known (refer to the Patent Literature 4).

CITATION LIST

Patent Literature

PTL 1. Japanese Laid-Open Patent Application Publication No. 2007-111004
PTL 2. Japanese Laid-Open Patent Application Publication No. 2006-288336
PTL 3. Japanese Laid-Open Patent Application Publication No. 2006-204241
PTL 4. Japanese Laid-Open Patent Application Publication (Translation of PCT application) No. 2005-530517

SUMMARY OF INVENTION

Technical Problem

However, as described above, though there is a document reporting a technology of transporting a specified DNA and the like, there is no document reporting a technology of transporting a specified antigen.

The main object of the present invention is to provide a technology for concentrating and detecting a target molecule by effectively transporting a target antigen.

Solution to Problem

As a result of intensive studies to achieve the above described object, the present inventors have found that a substance being produced from a living body in response to changes in the external environment can be efficiently transported, concentrated and detected, and the present invention has been completed.

(1) A motor protein device according to the present invention includes: a collection region, wherein a carrier molecule collects a target molecule by using an antigen-antibody reaction; and an unloading region, wherein the target molecule is unloaded from the carrier molecule by using a chemical equilibrium.

(2) Further, the motor protein device according to the present invention includes: a collection region, wherein a carrier molecule collects a target molecule by using an antigen-antibody reaction; and an unloading region, wherein a complex including the target molecule is unloaded from the carrier molecule by using a chemical equilibrium.

(3) Further, the motor protein device according to claim (1) or (2), further includes a transport path, wherein the transport path is provided between the collection region and the unloading region, and the carrier molecule is capable of transporting the target molecule through the transport path.

(4) Further, the motor protein device according to any one of claims (1) to (3), wherein the motor protein device is connected to an analysis portion for detecting the change in concentration of the target molecule in the unloading region.

(5) The motor protein device according to any one of claims (1) to (4), wherein the carrier molecule includes a partial structure as a predetermined antibody capable of binding with a predetermined antigen.

(6) The motor protein device according to any one of claims (1) to (5), wherein the unloading region includes a substance having a higher binding capability to the target molecule with a capture force, than the binding capability of the predetermined antibody being modified to the carrier molecule.

(7) The motor protein device according to any one of claims (3) to (6), wherein the transport path immobilized a protein to move the carrier molecule by interacting with the carrier molecule.

(8) The motor protein device according to any one of claims (3) to (7), wherein the carrier molecule includes a molecule of a modified predetermined antibody, and the transport path, on the surface, includes a motor protein being immobilized.

(9) The motor protein device according to any one of claims (1) to (8), wherein the predetermined antibody has binding capability with at least one target molecule.

(10) The motor protein device according to any one of claims (4) to (9), wherein the analysis portion includes an electrical detection means of the target molecule in the unloading region.

(11) The motor protein device according to any one of claims (4) to (9), wherein the analysis portion includes an optical detection means of the target molecule in the unloading region.

(12) The motor protein device according to any one of claims (1) to (11), wherein the target molecule is a tumor marker.

(13) A cancer sensor array comprises the motor protein device according to claim (12).

By the constitution as these, with regard to the motor protein device according to the present invention, the carrier molecule can collect the target molecule by using the antigen-antibody reaction in the collection region, and the carrier molecule can unload the target molecule by the chemical equilibrium in the unloading region. Because the unloading region contains a predetermined antibody having a higher capture force in a unit surface area than the antibody modified to the carrier molecule, the motor protein device according to the present invention can concentrate the target molecule in the unloading region by transporting the target molecule one after another with the carrier molecule and by unloading it in the unloading region.

Advantageous Effects of Invention

The motor protein device according to the present invention can detect the target molecule by effectively transporting it. Further, the motor protein device according to the present invention can detect the target molecule with high sensitivity by concentrating the target molecule in the unloading region.

DESCRIPTION OF EMBODIMENTS

Figure 1:
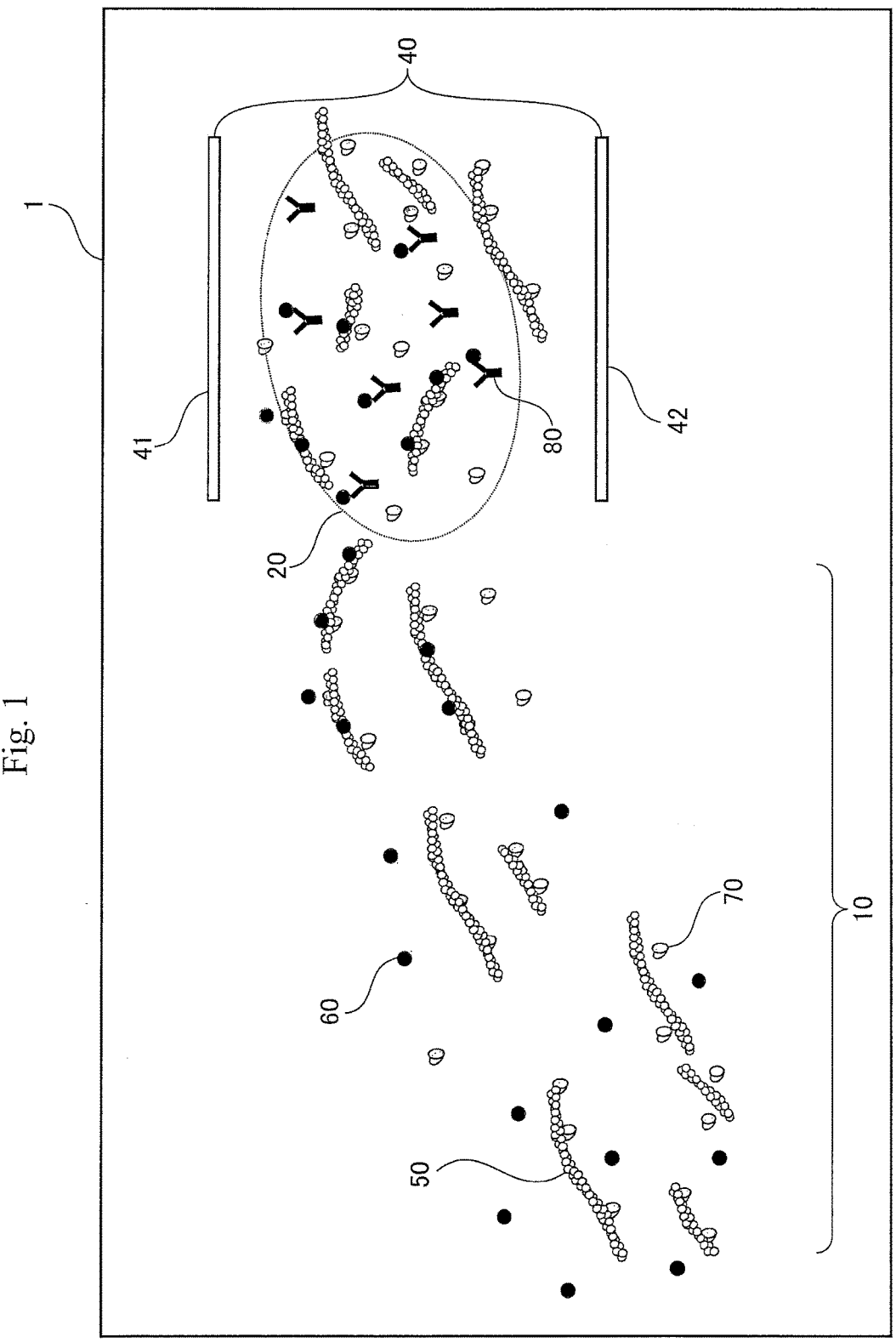
FIG. 1 A diagram exemplifying a basic component of a motor protein device according to one embodiment of the present invention.

FIG. 1 is a diagram exemplifying a basic structure of a motor protein device according to one embodiment of the present invention.

The motor protein device 1 includes a collection region 10 and an unloading region 20. These regions are, for example, provided on a substrate which is capable of immobilizing a protein, and are filled with a buffer solution or the like. Further, the buffer solution can contain ATP (adenosine triphosphate) or the like for activating the motor protein, if necessary.

The collection region 10 is a region where a carrier molecule 50 collects a target molecule 60 by using an antigen-antibody reaction. The carrier molecule 50 can be modified in advance with an antibody capable of binding to a predetermined antigen.

As an example, the carrier molecule 50 can contain an actin obtained by modifying a predetermined antibody, and the collection region 10 and the unloading region 20 can contain an immobilized myosin.

The target molecule 60 refers to a molecule to be an object for concentrating and detecting, in the concentration and detection using the antigen-antibody reaction. The target molecule 60 is not specifically limited as long as it is collected by the carrier molecule 50. The target molecule 60 can include a derivative of the target molecule 60 obtained by chemically modifying it, and a substance obtained by modifying an antigen site 61 of the target molecule 60 which is capable of binding to a predetermined antibody (refer to FIG. 2 (c)). As an example, a protein, a peptide, a sugar, a lipid, a nucleic acid or the like can be included. In addition, an antigen, an immunoglobulin, a tumor marker, a ligand, a virus, a bacteria or the like can be included.

The unloading region 20 is an region where the target molecule 60 is unloaded from the carrier molecule 50 by using a chemical equilibrium. The unloading region 20 can include a substance having binding capability for the target molecule 60 or a predetermined antigen, where the substance has a higher capture force or a higher concentration than a predetermined antibody being modified with the carrier molecule 50 in a unit surface area. As an example, the unloading region 20 includes an antibody 80 capable of binding to the target molecule 60, where the antibody 80 has a higher capture force or has a higher concentration than the capture force or the concentration of the carrier molecule 50, and thereby it is possible to unload the target molecule 60 from the carrier molecule 50 by using the chemical equilibrium.

Further, the motor protein device 1 can be connected to an analysis portion 40 for detecting the change in concentration of the target molecule 60 in the unloading region 20, and can detect that the target molecule 60 is unloaded in the unloading region 20. For example, the analysis portion 40 includes electrodes 41, 42 as a part of an electrical detection means, and an impedance or a change in the impedance of the unloading region 20 can be detected through the electrodes 41, 42. That is, in the motor protein device 1, it is possible to detect the change in concentration of the target molecule 60 in the unloading region 20 as the impedance or the change in the impedance of the unloading region 20.

As an example, the predetermined antibody can have a binding capability for at least one immunoglobulins.

By configuring as these, the carrier molecule 50 of the motor protein device 1 can move to the unloading region 20, after collecting the immunoglobulins as the target molecule 60 by using the antigen-antibody reaction, in the collection region 10. Because an antibody having a higher capture force or a higher concentration than the capture force or the concentration of the antibody being modified to the carrier molecule 50 is included in the unloading region 20, the immunoglobulin as the target molecule 60 binds to the antibody in the unloading region 20 by the chemical equilibrium. That is, the carrier molecule 50 can unload the target molecule 60 in the unloading region 20. With the passage of time, the carrier molecule 50 continues to unload the immunoglobulin in the unloading region 20 one after another, the immunoglobulin is concentrated in the unloading region 20. This concentration of the immunoglobulin can be detected by the analysis portion 40 as the change in the impedance of the unloading region 20.

Figure 2:
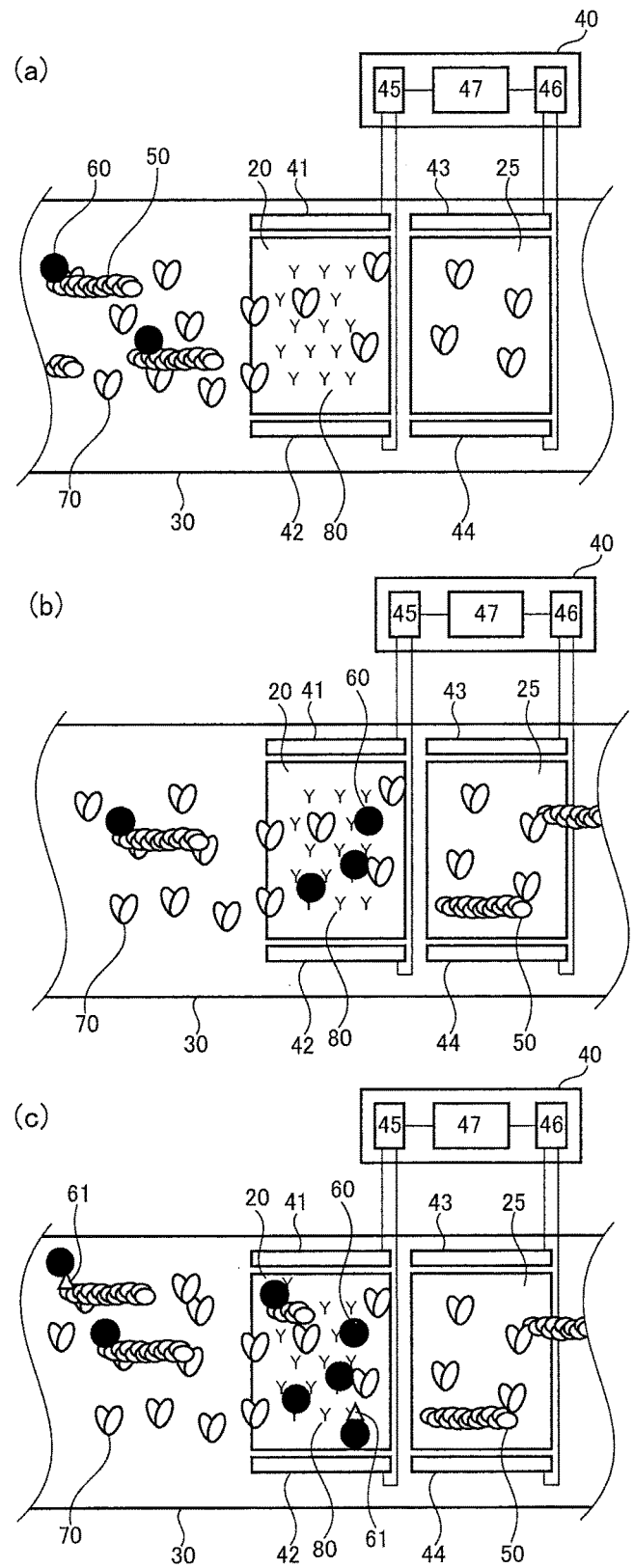
FIG. 2 A diagram illustrating to explain that the motor protein device according to one embodiment of the present invention concentrates a target molecule.

FIG. 2 is a diagram to explain that the motor protein device according to one embodiment of the present invention concentrates a target molecule. FIG. 2(a) is a diagram to explain the movement of the carrier molecule 50 to the unloading region 20, FIG. 2(b) and FIG. 2(c) are diagrams to explain that the carrier molecule 50 unload the target molecule 60 in the unloading region 20.

In FIG. 2(a), the carrier molecule 50 transports the collected target molecule 60 along a transport path 30. The transport path 30 is, for example, a passage provided between the above described collection region and the unloading region 20, and can contain an immobilized myosin 70 and the like such as in the collection region 10. Meanwhile, the transport path 30 can be a passage independent from the collection region 10, or a part of the collection region 10 or the unloading region 20. The transport path 30 can consist of a plurality of passages to reach the unloading region 20.

The analysis portion 40 exemplified in FIG. 2(a) includes analysis circuits 45, 46, 47 as an electrical detection means. The analysis circuit 45 is used to measure the impedance of the unloading region 20 via the electrodes 41, 42. The analysis circuit 46 is used to measure the impedance of a reference region 25 via the electrodes 43, 44. The reference region 25 is provided similarly with the unloading region 20, except that it does not include the above described antibody 80. The analysis circuit 47 is used for measuring the difference between the impedance of the unloading region 20 which is measured by the analysis circuit 45 and the impedance of the reference region 25 which is measured by the analysis circuit 46.

In FIG. 2(b), the antibody 80 having a higher capture force or a higher concentration than the capture force or the concentration of the carrier molecule 50 is immobilized in the unloading region 20. Accordingly, when the carrier molecule 50 reaches the unloading region 20, the target molecule 60 which binds to the antibody 80 increases as compared to the target molecule 60 which binds to the carrier molecule 50 by a chemical equilibrium. In other words, the target molecule 60 is unloaded from the carrier molecule 50 in the unloading region 20. In the unloading region 20 and the reference region 25, the immobilized myosin 70 is included, and the carrier molecule 50 passes through these regions after unloading, without retenting in the unloading region 20. The following carrier molecule 50 can reach the unloading region 20 continuously.

In this way, the target molecule 60 is unloaded one after another as time passes, and is concentrated in the unloading region 20. In accordance with the increase in the concentration of the target molecule 60 in the unloading region 20, a capacitance component of the impedance of the unloading region 20 increases. On the other hand, because the target molecule 60 is not concentrated in the reference region 25, the impedance of the reference region 25 does not change substantially. Accordingly, the increase in the concentration of the target molecule 60 in the unloading region 20 can be detected as a change in the impedance of the unloading region 20 which is measured by the analysis circuit 45, or as a change in the difference of the impedance between the reference region 25 and the unloading region 20 which is measured by the analysis circuit 47.

Further, as exemplified in FIG. 2(c), even a complex which is a target molecule 60 bound to a part of the carrier molecule 50 or which includes a target molecule 60 with an modified antigen site 61, the capacitance component of the impedance of the unloading region 20 increases, and so the increase in the concentration of the target molecule 60 in the unloading region 20 can be detected.

In FIGS. 2(a), (b) and (c), one piece of transport path 30, a pair of electrodes 41, 42 and a pair of electrodes 43, 44 in the reference region 25 are exemplified, but without being limited to these, the aspect such as the number of the transport path 30 and the arrangement, the shape and the like of the electrodes for the impedance measurement can be designed arbitrarily.

Figure 3:
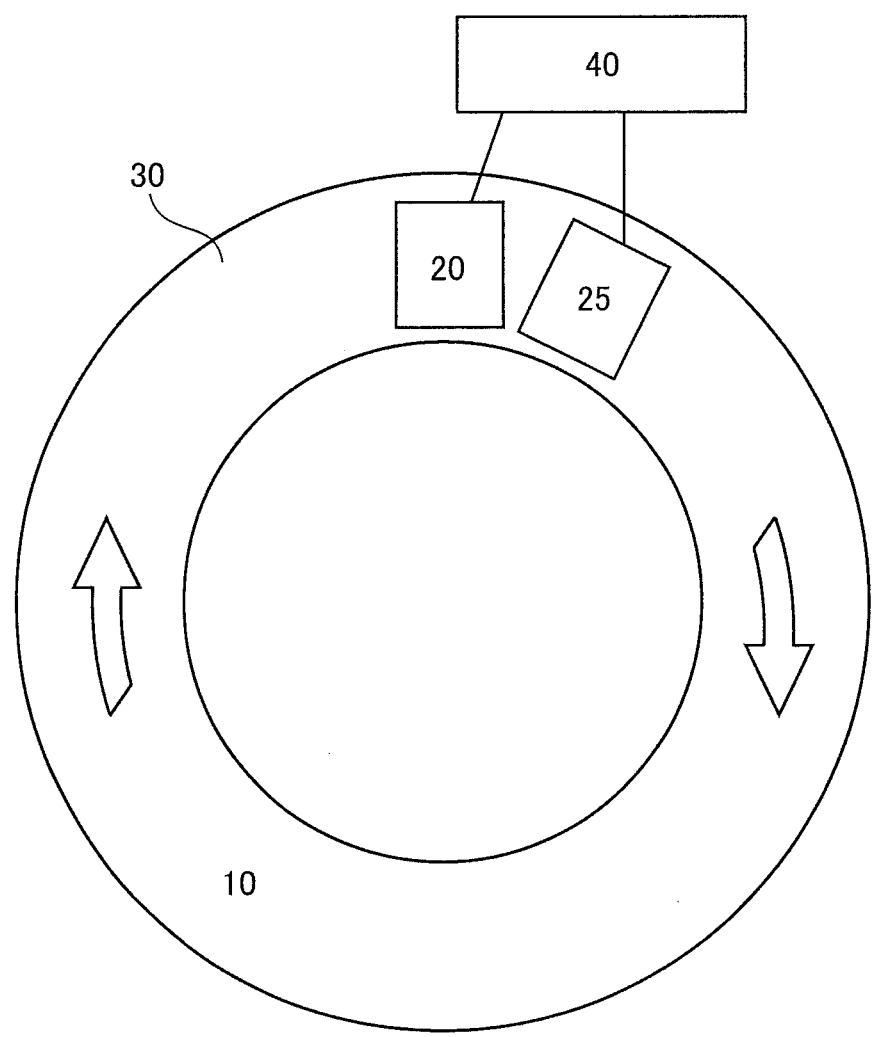
FIG. 3 A diagram illustrating an example of a transport path of the motor protein device according to one embodiment of the present invention.

FIG. 3 is a diagram illustrating an example of a transport path of the motor protein device according to one embodiment of the present invention.

In FIG. 3, the transport path 30 has a shape of an annular passage as a whole, and the immobilized myosin 70 is included on the entire surface of the transport path 30 which is the annular passage. The carrier molecule which collected the target molecule 60 in the collection region 10 can return to the collection region 10 again along the path of the transport path 30 after unloading the target molecule 60 in the unloading region 20. Accordingly, the carrier molecule 50 can repeat to collect the target molecule 60, transport it to the unloading region 20 and unload it there, and can continue to concentrate the target molecule 60.

Such a movement of the carrier molecule 50 is possible by a chemical energy source such as ATP and a like which exists in a buffer solution without the need to provide a mechanism for flowing the buffer solution. Therefore, the motor protein device according to the present invention can be configured as a concentration means of a target molecule 60 which is operable without power.

Figure 4:
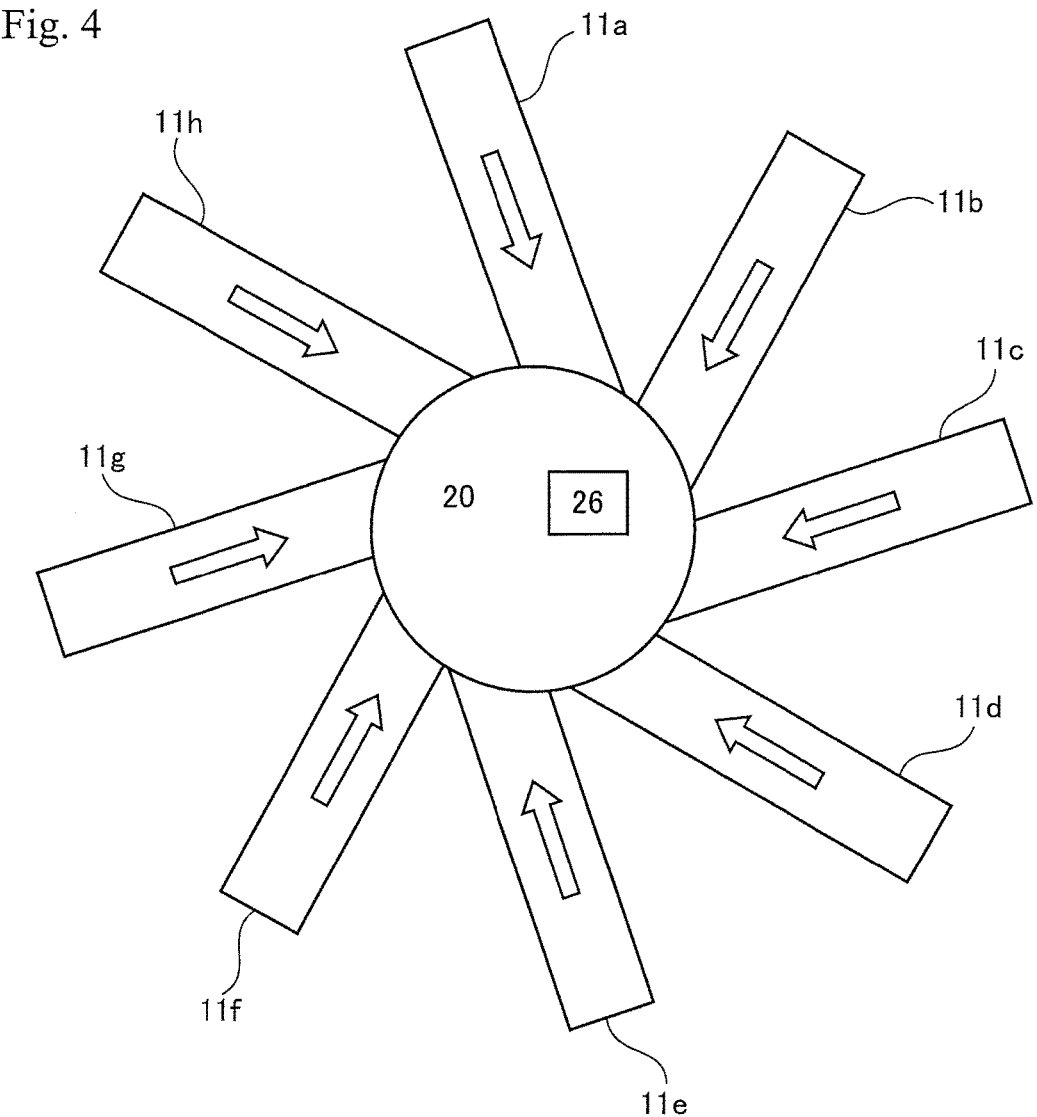
FIG. 4 A diagram illustrating another embodiment of the motor protein device according to one embodiment of the present invention.

FIG. 4 is a diagram illustrating another embodiment of the motor protein device according to one embodiment of the present invention.

In FIG. 4, the unloading region 20 is provided as a common region for unloading for a plurality of motor protein devices 11a-h. Each of the motor protein devices 11a-h is configured to carry the target molecule toward the unloading region 20, and unload there. Accordingly, in the unloading region 20 shown in FIG. 4, each of the motor protein devices 11a-h continues to unload the target molecule 60, and thereby the target molecule 60 is concentrated in a short time.

In the unloading region 20 shown in FIG. 4, a light path 26 for connecting a predetermined means for optically detecting a change in the concentration of the target molecule 60 can be provided. The light path 26 is composed of a transmitting material and the like which can pass through the light of a specific wavelength range, for example. A change in the concentration of the target molecule 60 can be detected as a change in the absorption rate at a specific wavelength through the light path 26 of the buffer solution in the unloading region 20.

Though the light path 26 for an optical detection means is exemplified in FIG. 4, not limited to this, using the analysis portion 40 and the electrodes 41 to 44 as an electrical detection means shown in FIGS. 1 to 3 optionally, it is possible to detect a change in the concentration of the target molecule 60 in the unloading region 20 shown in FIG. 4.

Figure 5A:
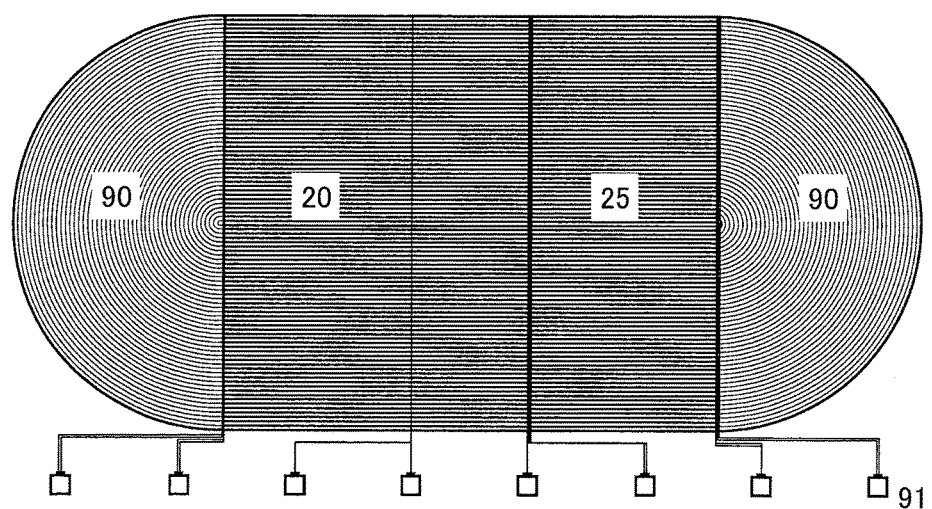
FIG. 5 A diagram exemplifying a cancer sensor array equipped with the motor protein device according to one embodiment of the present invention.
Figures 5B, 6:
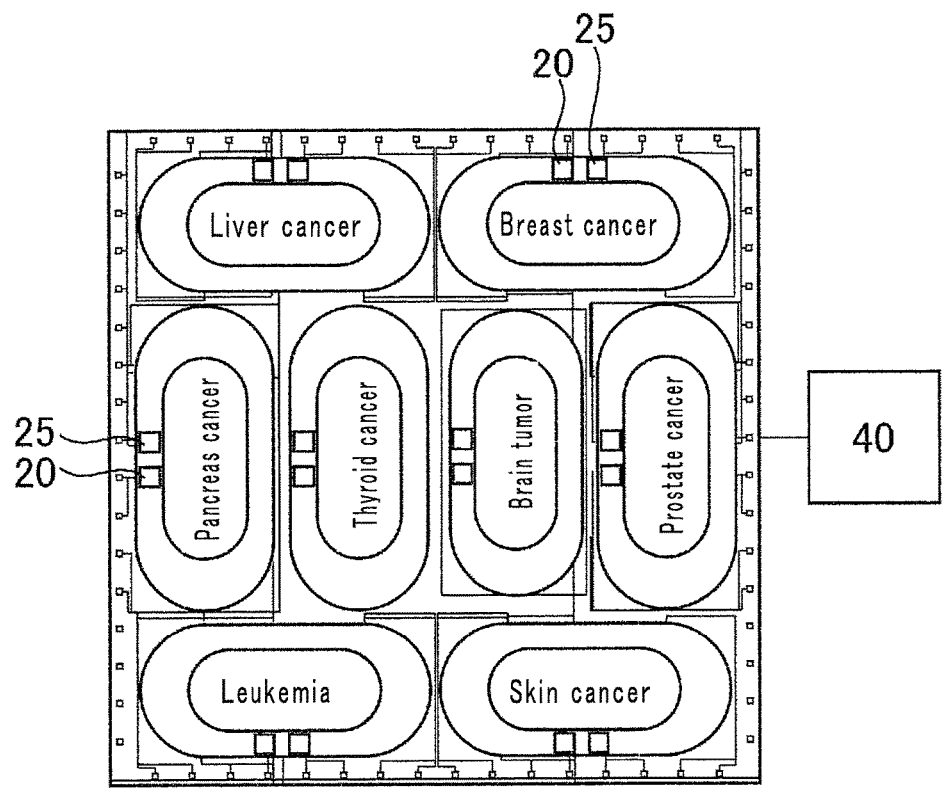
FIG. 6 A diagram representing evaluation results of a device according to one embodiment of the present invention and of a device of a conventional method.

FIG. 5 is a diagram illustrating an example of a cancer sensor array comprises the motor protein device according to one embodiment of the present invention. In the cancer sensor array, the target molecule 50 is a tumor marker. FIG. 5(a) is a diagram to explain a structure of a Si semiconductor substrate which is a cancer sensor array, and FIG. 5(b) is a diagram exemplifying a cancer sensor array including a motor protein device.

When a specimen which seems to include the target molecule 60 is placed on a loading region 90 of the cancer sensor array, the actin of the carrier molecule 50 transports the collected tumor marker, and unloads the tumor marker in the unloading region 20. In the unloading region 20, the tumor marker is unloaded one after the other with the passage of time, and is concentrated. On the other hand, because the tumor marker is not concentrated in the reference region 25, an increase in the concentration of the target molecule 60 in the unloading region 20 can be detected as a change in the impedance of the unloading region 20 which is measured by the analysis circuit 45 included in the analysis portion 40, or as a change in the difference of the impedance between the reference region 25 and the unloading region 20 which is measured by the analysis circuit 47.

And, as exemplified in FIG. 5(b), the cancer sensor array can take a structure in which a plurality of motor protein devices are stacked, and can detect a plurality of tumor markers at the same time and with high efficiency.

As an example of the specimen, a specimen prepared from blood, serum, plasma, urine, sweat, sputum, prostatic fluid, gastric fluid, intestinal fluid, renal fluid, lung fluid, cerebrospinal fluid, spinal fluid, sperm and the like, or a specimen prepared from a tissue of brain, esophagus, stomach, lung, small intestine, large intestine, pancreas, liver, kidney, bladder, spleen, thyroid, testis, uterus, bone and the like can be included. In addition, as an example of a tumor marker, AFP, BCA225, CA15-3, CA19-9, CA72-4, CA125, CEA, CYFRA, DUPAN-2, NMP22, NSE, PA (PSA), PIVKA-II, ProGRP, SCC can include SLX, TPA, γ-Sm, anti-p53 antibody, elastase 1 and the like can be included.

(Manufacturing of Si Semiconductor Substrate)

The cancer sensor array according to the present invention is described using FIG. 5(a). A Si semiconductor substrate having a surface structure with a track-like flow path, as exemplified in FIG. 5(a), was manufactured by the standard CMOS process. Here, the flow path width of the unloading region 20 and the reference region 25 was 1.2 μm and the flow path width of the arc of the loading region 90 was 10 μm. A counter electrode using a metal wiring layer and an electrode pad 91 was formed on the flow path of the unloading region 20 and the reference region 25.

(Surface Treatment of Si Semiconductor Substrate)

The obtained Si semiconductor substrate was subjected to ultrasonic cleaning with isopropyl alcohol for 1 hours, and was dried by heating at 60 degree C. for 2 hours in a dust free environment. Then, a surface coating agent (made by Shin-Etsu Chemical Co., Ltd., KJC7022) was adjusted to 0.001 mg/mL, and was coated on the Si semiconductor substrate with a spin coater. This was dried by heating at 60 degree C. for 5 hours in the dust-free environment, and the surface of the Si semiconductor substrate was subjected to hydrophobic treatment.

(Surface Treatment of Cover Glass)

A cover glass covering the unloading region 20 and the reference region 25 was subjected to ultrasonic cleaning in a cleaning solution (0.1M KOH+70% ethanol) for 1 hour, and then the cover glass was further washed with pure water. The cover glass was dried by heating at 60 degree C. for 5 hours in the dust-free environment, and the surface of the cover glass was hydrophilized.

(Printing of Motor Protein)

A solution prepared by adding 20 μg/mL of cover protein to the motor protein solution of pH=8.0 which is obtained by diluting 26 μg/mL of skeletal muscle myosin with 25 mM KCl, 3.0 mM $MgCl_2$ and 5.0 mM pH buffer solution (Tris-HCl), and the solution was printed on the entire track of the Si semiconductor substrate by an inkjet method.

(Printing of Antibody 80 to Unloading Region 20)

An anti-human CEA monoclonal antibody (1.0 mg/mL) which was a tumor marker of early lung cancer was selected as the antibody 80, and was printed on the unloading region 20 by an inkjet method.

(Adjustment of Transport Unit Protein)

Using a Sephadex G-25, 0.5 mL of 1.0 mg/mL anti-human CEA monoclonal antibody was adjusted with 50 mM of phosphate buffer solution. The SM(PEG)12 (made by THERMO SCIENTIFIC Co., Ltd.) which was a cross-linking agent of 2000-fold amount was added to this and the reaction was made at 25 degree C. for 3 hours. Further, after adding the Tris-HCl in an amount corresponding to 50-fold amount of the SM (PEG) 12, adjustment was made with 50 mM of phosphate buffer solution. To this, 0.5 mL of skeletal muscle actin fiber solution (diluted 1.0 mg/mL of skeletal muscle actin fiber with 25 mL of KCl, 2.0 mM of ATP, 0.1 mM of $CaCl_2$, 10 mM of creatine phosphate sodium and 10 mg/mL creatine kinase) was added, and after heat treating at 25 degree C. for 3 hours, 2-mercaptoethanol in an amount corresponding to 50-fold amount of the SM(PEG)12 was added, and thereby the transport unit protein was adjusted.

(Preparation of Carrier Molecule 50 and Injection Thereof into Si Semiconductor Substrate)

The protein transport unit and the skeletal muscle actin filament were mixed at a ratio of 1:10000 in a solvent (25 mM KCl, 25 mM imidazole-HCl (pH=7.4), 2.0 mM $MgCl_2$, mM ATP, 1 mM DTT, 10 mM creatine phosphate, 100 U/mL creatine kinase), and thereby a nano transport fiber which was the carrier molecule 50 is obtained. On a Si semiconductor substrate, 15 μL of the nano transport fiber was dropped. Further, 2.0 μL thereof was dropped and 2.0 μL of the solution on the surface was subjected to suction cleaning. On the Si semiconductor substrate, a diethylaminoethyl (DEAE) ion exchange membrane was mounted, and the ambient moisture was aspirated. The cover glass which was subjected to surface treatment was mounted thereto and was adhered under pressure using a hydrophilic adhesive.

(Impedance Measurement and Comparison with Conventional Method)

To the cancer sensor array, 2.0 μL of artificial serum containing 0.10 ng/mL to 100 ng/mL of the tumor marker CEA was dropped. Using the semiconductor circuit of the sensor unit, the impedance measurement was performed. The measurement was carried out by a parallel four terminal method. The changes in the impedance of the unloading region 20 and the reference region 25 were differentially detected and the output value was converted to a voltage. Further, as a comparative example, the tumor marker CEA was detected using a chemiluminescence immunoassay. Both results are shown in FIG. 6. From the result, it has been found that early cancer detection capability according to the present invention is equivalent to those of the conventional methods, and the present invention can be performed at low cost and at high speed because the measurement thereof can be made electrically.

As mentioned above, while the present invention has been described with reference to the embodiments, it is needless to say that the technical scope of the present invention is not limited to the scope described in the above embodiments. It is apparent to those skilled in the art that various changes or modifications can be added to the embodiments described above. In addition, it is apparent from the description in the appended claims that the embodiments added with such changes or improvements can be included in the technical scope of the present invention.

REFERENCE SIGNS LIST 1, 11 motor protein device
10 collection region
20 unloading region
25 reference region
26 light path
30 transport path
40 analysis portion
41, 42, 43, 44 electrode
45, 46, 47 analysis circuit
50 carrier molecule
60 target molecule
61 antigen site
70 immobilized myosin
80 antibody 90 loading region
91 electrode pad

The invention claimed is:

1. A motor protein device comprising:
a collection region in which a carrier molecule comprising an actin collects a target molecule using an antigen-antibody reaction;
an unloading region in which the target molecule is unloaded from the carrier molecule by using a chemical equilibrium; and
a transport path provided between the collection region and the unloading region, through which the carrier molecule is capable of transporting the target molecule, and in which a myosin as a motor protein is immobilized on the transport path so as to interact with the carrier molecule to move the carrier molecule through the transport path, wherein
the carrier molecule further comprises, as a partial structure, a predetermined antibody capable of binding with a predetermined antigen.

2. A motor protein device comprising:
a collection region in which a carrier molecule comprising an actin collects a target molecule by using an antigen-antibody reaction; and
an unloading region in which a complex comprising the target molecule is unloaded from the carrier molecule by using a chemical equilibrium; and
a transport path provided between the collection region and the unloading region, through which the carrier molecule is capable of transporting the target molecule, and in which a myosin as a motor protein is immobilized on the transport path so as to interact with the carrier molecule to move the carrier molecule through the transport path, wherein
the carrier molecule further comprises, as a partial structure, a predetermined antibody capable of binding with a predetermined antigen.

3. The motor protein device according to claim 1, wherein the motor protein device is connected to an analysis portion for detecting a change in concentration of the target molecule in the unloading region.

4. The motor protein device according to claim 1, wherein the unloading region comprises a substance having a target molecule-binding capability higher than that of the predetermined antibody contained in the carrier molecule.

5. The motor protein device according to claim 1, wherein the carrier molecule comprises a molecule of a modified predetermined antibody, and the transport path comprises the immobilized motor protein throughout a surface thereof.

6. The motor protein device according to claim 1, wherein the predetermined antibody has binding capability with at least one target molecule.

7. The motor protein device according to claim 3, wherein the analysis portion comprises a means for electrically detecting the target molecule in the unloading region.

8. The motor protein device according to claim 3, wherein the analysis portion comprises a means for optically detecting the target molecule in the unloading region.

9. The motor protein device according to claim 1, wherein the target molecule is a tumor marker.

10. A cancer sensor array comprising the motor protein device according to claim 9.

11. A motor protein device comprising:
a collection region in which a carrier molecule collects a target molecule using an antigen-antibody reaction;
an unloading region in which the target molecule is unloaded from the carrier molecule by using a chemical equilibrium; and
a transport path provided between the collection region and the unloading region, through which the carrier molecule is capable of transporting the target molecule, and in which a motor protein is immobilized on the transport path so as to interact with the carrier molecule to move the carrier molecule through the transport path,
wherein the transport path is configured to return the carrier molecule to the collection region after unloading the target molecule in the unloading region,
the carrier molecule returning to the collection region after unloading the target molecule in the unloading region is used again for collecting another target molecule in the collection region, and
the carrier molecule comprises, as a partial structure, a predetermined antibody capable of binding with a predetermined antigen.

12. The motor protein device according to claim 11, wherein the transport path is annularly shaped.

* * * * *